United States Patent
Dixon et al.

(10) Patent No.: US 11,311,471 B2
(45) Date of Patent: *Apr. 26, 2022

(54) METHODS, COMPOSITIONS AND USES RELATING THERETO

(71) Applicant: INNOSPEC LIMITED, Ellesmere Port (GB)

(72) Inventors: Nicholas John Dixon, Chester (GB); Matthew Robert Giles, Chester (GB); Kimberley Elizabeth Griffiths, Denbighshire (GB); Tony Gough, Chester (GB); Ian Malcolm McRobbie, Chester (GB)

(73) Assignee: Innospec Limited, Cheshire (GB)

( * ) Notice: Subject to any disclaimer, the term of this patent is extended or adjusted under 35 U.S.C. 154(b) by 21 days.

This patent is subject to a terminal disclaimer.

(21) Appl. No.: 16/337,504

(22) PCT Filed: Sep. 29, 2017

(86) PCT No.: PCT/GB2017/052929
§ 371 (c)(1),
(2) Date: Mar. 28, 2019

(87) PCT Pub. No.: WO2018/060727
PCT Pub. Date: Apr. 5, 2018

(65) Prior Publication Data
US 2020/0030212 A1   Jan. 30, 2020

(30) Foreign Application Priority Data

Sep. 30, 2016  (GB) ..................... 1616666

(51) Int. Cl.
| | | |
|---|---|---|
| *A61K 8/49* | (2006.01) | |
| *A61K 8/34* | (2006.01) | |
| *A61K 8/41* | (2006.01) | |
| *A61K 8/44* | (2006.01) | |
| *A61Q 5/02* | (2006.01) | |
| *A61Q 5/04* | (2006.01) | |
| *A61Q 5/06* | (2006.01) | |
| *A61Q 5/10* | (2006.01) | |
| *A61Q 5/12* | (2006.01) | |

(52) U.S. Cl.
CPC .............. *A61K 8/4913* (2013.01); *A61K 8/34* (2013.01); *A61K 8/41* (2013.01); *A61K 8/44* (2013.01); *A61K 8/494* (2013.01); *A61Q 5/02* (2013.01); *A61Q 5/04* (2013.01); *A61Q 5/06* (2013.01); *A61Q 5/10* (2013.01); *A61Q 5/12* (2013.01); *A61K 2800/43* (2013.01)

(58) Field of Classification Search
CPC ........ A61K 8/4913; A61K 8/494; A61K 8/44; A61K 8/41; A61K 8/34; A61K 2800/43; A61K 8/361; A61K 8/33; A61K 2800/51; A61K 8/362; A61Q 5/12; A61Q 5/10; A61Q 5/06; A61Q 5/04; A61Q 5/02; A61Q 5/004; D06M 13/402; D06M 13/342; D06M 13/127; D06M 13/12; D06M 13/432; D06P 1/6426; D06P 1/6495; D06P 1/65112; D06P 1/647; D06P 3/14; D06P 5/08; D06P 5/04; D06P 3/148; D06P 1/6496; D06P 5/06; D06P 1/649

See application file for complete search history.

(56) References Cited

U.S. PATENT DOCUMENTS

| | | | |
|---|---|---|---|
| 4,486,328 A | 12/1984 | Knott | |
| 5,833,966 A | 11/1998 | L'Oreal | |
| 2004/0187226 A1 | 9/2004 | Muerner | |
| 2011/0117147 A1* | 5/2011 | Ishida | C07C 69/24 424/401 |
| 2015/0034117 A1 | 2/2015 | Pressly et al. | |
| 2015/0034119 A1 | 2/2015 | Pressly et al. | |
| 2019/0091120 A1* | 3/2019 | Gough | C07C 47/19 |
| 2019/0231664 A1* | 8/2019 | Dixon | A61K 8/41 |
| 2019/0269591 A1* | 9/2019 | Dixon | A61K 8/361 |
| 2020/0030211 A1* | 1/2020 | Dixon | D06P 1/6426 |

FOREIGN PATENT DOCUMENTS

| | | |
|---|---|---|
| CN | 104758213 A | 7/2015 |
| DE | 10048922 A1 | 4/2002 |
| EP | 0305128 A1 | 3/1989 |
| EP | 2005939 A1 | 12/2008 |
| FR | 2937543 A1 | 4/2010 |
| FR | 3017797 A1 | 8/2015 |
| GB | 981825 A | 1/1965 |
| JP | 04112820 A | 4/1992 |
| JP | 2009263319 A | 11/2009 |
| KR | 20130114468 A | 10/2013 |
| WO | 9827941 A1 | 7/1998 |

(Continued)

OTHER PUBLICATIONS

English translation of FR2937543 (Year: 2008).*
Verhovnik et al., "SILSOFT A-553 Conditioning Agent and SILSOFT A-454 Colour Retaining Conditioning Agent: New Dimethicone Conditioners For Hair Care" EURO-COSME, Heidelberg, DE, No. 3, Jan. 1, 2002 (Jan.1 2002), pp. 20-25, ISSN: 0944-8942.
International Search Report and Written Opinion dated Jan. 31, 2018 for Application No. PCT/GB2017/052929.
Database GNPD [Online] Mintel; Jun. 1, 2015, "Hair Treatment", Database accession No. 3255661.

(Continued)

*Primary Examiner* — Quanglong N Truong
(74) *Attorney, Agent, or Firm* — Carlos A. Fisher; Stout, Uxa & Buyan, LLP

(57) ABSTRACT

A method of treating a material, the method comprising the steps of: (1) contacting the material with a composition comprising an electrophilic species selected from aldehydes, succinimidyl esters, and mixtures thereof; (2) contacting the material with a composition comprising a chelating agent and/or a salt of an amine and/or a carboxylic acid.

16 Claims, No Drawings

(56) References Cited

FOREIGN PATENT DOCUMENTS

| WO | WO-0230373 A2 * | 4/2002 | ............... A61Q 5/10 |
|----|----|----|----|
| WO | 2008151273 A2 | 12/2008 | |
| WO | 2015074971 A1 | 5/2015 | |
| WO | 2018060719 A1 | 5/2018 | |
| WO | 2018060720 A1 | 5/2018 | |

OTHER PUBLICATIONS

Database GNPD [Online] Mintel; Sep. 1, 2009, "Colour effect shampoo", Database accession No. 1182152.
Database GNPD [Online] Mintel; Nov. 1, 2004, "Illuminating Color Protection Styling Products", Database accession No. 10197511.
International Preliminary Report on Patentability dated Apr. 11, 2019 for International Application No. PCT/GB2017/052929.

* cited by examiner

METHODS, COMPOSITIONS AND USES RELATING THERETO

CROSS-REFERENCE TO RELATED APPLICATIONS

This application is a U.S. national stage application under 35 U.S.C. 371 of co-pending International Application No. PCT/GB2017/052929, filed on Sep. 29, 2017, and entitled METHODS, COMPOSITIONS AND USES RELATING THERETO, which in turn claims priority to and benefit of Great Britain Patent Application No. 1616666.2, filed on Sep. 30, 2016, which are incorporated by reference herein in their entirety for all purposes.

The present invention relates to a method of treating a material, to compositions for use in such methods and to uses relating thereto. In particular the present invention relates to a method of treating a keratinous material, especially hair, to provide a benefit to the material.

The appearance, condition and cleanliness of their hair are of great significance to many people. As a result there is a vast array of hair care products available offering a wide range of benefits and containing a huge number of different components. However popular hair styles change continually with fashion trends and technological developments in hair styling appliances means that there is a continuing need for different and improved hair care compositions. Furthermore as we learn more about the toxicity of certain chemicals and their environmental impact there is an increasing requirement to take these considerations into account when developing cosmetic products.

For example one previously used constituent of cosmetic hair care compositions is formaldehyde. However formaldehyde is a suspected carcinogen and thus its use in cosmetic compositions is now strictly regulated and highly undesirable.

The appearance, condition and cleanliness of textiles and fabric materials is also of considerable importance and the stresses encountered by these materials in the environments in which they are used may have a deleterious effect on them.

It is an aim of the present invention to provide means for enhancing at least one property of a material.

According to a first aspect of the present invention there is provided a method of treating material, the method comprising the steps of:
(1) contacting the material with a composition comprising an electrophilic species selected from aldehydes, succinimidyl esters and mixtures thereof;
(2) contacting the material with a composition comprising a chelating agent and/or a salt of an amine and a carboxylic acid.

Steps (1) and (2) may be carried out in any order. They may be carried out sequentially or simultaneously. In some embodiments step (1) is carried our before step (2). In some embodiments step (2) is carried out before step (1).

In preferred embodiments steps (1) and (2) are carried out simultaneously and the method of the present invention involves contacting the material with a composition comprising an electrophilic species selected from aldehydes, succinimidyl esters and mixtures thereof and a chelating agent and/or a salt of an amine and a carboxylic acid.

For the avoidance of doubt when we refer to "a salt of an amine and a carboxylic acid" we mean to refer to the reaction product of an amine and a carboxylic acid and thus the amine salt of a carboxylic acid. The salt comprises an ammonium cation and a carboxylate anion.

The present invention relates to a method of treating a material. In some embodiments the material may be textile material. In such embodiments the textile material suitably comprises wool and preferably comprises wool as a major proportion thereof.

In preferred embodiments the material is a keratinous material. More preferably the material comprises keratinous fibres. Preferably the material is hair. The hair may be human or animal hair. In especially preferred embodiments the method of the present invention is a method treating human hair. Most preferably it is a method of treating human hair growing on the head.

However it will be appreciated that the method of the present invention can also be used to treat from hair that is not growing on the head, such as a wig or animal hair, for example wool.

The method of the present invention involves contacting the material, preferably hair, with a composition comprising an electrophilic species selected from one or more of an aldehyde and a succinimidyl ester and one or more of a chelating agent and a salt of an amine and a carboxylic acid.

According to a second aspect of the present invention there is provided a composition comprising: an electrophilic species selected from aldehydes, succinimidyl esters and mixtures thereof; and a chelating agent and/or a salt of an amine and a carboxylic acid.

Preferred features of the first and second aspects of the invention will now be described. Any feature may apply to any other aspect as appropriate. Thus the method of the first aspect may suitably involve contacting the hair with a composition comprising: an electrophilic species selected from aldehydes, succinimidyl esters and mixtures thereof; and a chelating agent and/or a salt of an amine and a carboxylic acid as defined in relation to the second aspect.

The invention will now be further described. Reference will be made to methods using a single composition comprising: an electrophilic species selected from aldehydes, succinimidyl esters and mixtures thereof; and a chelating agent and/or a salt of an amine and a carboxylic acid. However embodiments in which two or more compositions are used to achieve the same purpose are within the scope of the invention.

The composition of the second aspect of the present invention comprises an electrophilic species selected from aldehydes, succinimidyl esters and mixtures thereof.

For the avoidance of doubt by this we mean that the composition may comprise one or more than one aldehyde and no succinimidyl ester; no aldehydes and one or more than one succinimidyl esters; or one or more aldehydes and one or more succinimidyl esters.

Preferred aldehydes for use herein include hydroxyl-substituted aldehydes and alpha-substituted aldehydes. Aldehydes with a hydroxy substituent at the ∝-position are especially preferred.

Suitable aldehydes for use herein have at least 2 carbon atoms. Preferably they have at least 3 carbon atoms.

Suitable aldehydes for use herein may have up to 36 carbon atoms, preferably up to 30 carbon atoms, more preferably up to 24 carbon atoms, preferably up to 20 carbon atom, for example up to 18 carbon atoms or up to 16 carbon atoms.

Some preferred aldehydes for use herein have from 3 to 20 carbon atoms, for example 3 to 16 carbon atoms.

Some preferred aldehydes for use herein have from 3 to 12 carbon atoms, for example 3 to 11 carbon atoms.

Some especially preferred aldehydes for use herein have from 3 to 9 carbon atoms, more preferably from 3 to 8 carbon atoms.

Some other preferred aldehydes for use herein have from 8 to 16 carbon atoms, for example 10 to 14 carbon atoms.

In some preferred embodiments the aldehyde contains only one aldehyde functional group.

The aldehyde preferably has a substituent at the α-position and/or has a hydroxy substituent. It may have one or more further substituents.

Suitable further substituents may be selected from a further hydroxy substituent, a further aldehyde group, a keto group, a carboxy group, an acyl group, a halo group, an alkoxy group, an alkyl group, a nitro group, an amino group, a sulfoxy group, a mercapto group, an amide, an ester, a nitrile group or an isonitrile group.

Preferred halo substituents are chloro, fluoro, and bromo.

Preferred alkoxy substituents are methoxy, ethoxy, propoxy and butoxy, including isomers thereof.

Preferred alkyl substituents are $C_1$ to $C_8$ alkyl, preferably $C_1$ to $C_6$ alkyl, including isomers thereof.

In some embodiments the aldehyde may include a further aldehyde functional group.

Suitably such further aldehyde groups may be α-substituted.

In preferred embodiments the aldehyde includes a hydrocarbon chain. This is suitably a chain with a carbon backbone. However compounds in which the carbon backbone is interrupted by one or more heteroatoms are also within the scope of the invention. For example the carbon backbone may be interrupted by one or more oxygen, sulphur or nitrogen molecules and thus the aldehyde may include an ether, a thioether, an amine or a disulfide moiety.

The aldehyde may be predominantly aliphatic or predominantly aromatic in nature. Preferably the aldehyde is aliphatic. However it may include one or more double bonds and/or one or more cyclic groups. It may be straight-chain or branched.

In embodiments in which the aldehyde is hydroxy-substituted any suitable hydroxy substituted aldehyde may be included.

The aldehyde may comprise one or more hydroxy substituents.

Suitably the aldehyde comprises one, two or three hydroxy substituents, preferably one or two substituents.

In some preferred embodiments the aldehyde is not a saccharide.

Preferably the aldehyde comprises one hydroxy substituent.

Suitably the aldehyde has a hydroxyl substituent at the 2, 3 or 4 position.

In some embodiments the aldehyde may have a hydroxyl substituent at the 2 and 3 or the 2 and 4 positions.

Suitably the aldehyde may have a hydroxy substituent at the 2 position and/or the 3 position.

Suitably the aldehyde may have a hydroxy substituent at the 2 position or the 3 position.

In especially preferred embodiments the aldehyde has a hydroxy substituent at the 2 position. Thus the aldehyde is suitably an α-hydroxy aldehyde/a 2-hydroxy aldehyde.

The alpha-substituted aldehyde is suitably a compound of formula (I):

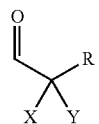

(I)

wherein X is selected from hydroxy, alkoxy, carboxy, alkylcarboxy, amino, nitro, mercapto, halo, keto, sulfoxy, alkyl, mercapto, amide, nitrile, isonitrile, ester and other carbonyl containing groups; Y is selected from hydrogen, hydroxy, alkoxy, carboxy, alkylcarboxy, amino, nitro, mercapto, halo, keto, sulfoxy, alkyl, mercapto, amide, nitrile, isonitrile, ester and other carbonyl containing groups; and R is hydrogen or an optionally substituted hydrocarbyl group having 1 to 36 carbon atoms.

In preferred embodiments Y is selected from hydrogen and a halogen. When Y is a halogen, X is suitably a halogen, for example X and Y may both be fluorine. In preferred embodiments Y is hydrogen.

Preferably the alpha-substituted aldehyde is a compound of formula (II):

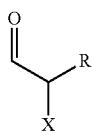

(II)

wherein X is selected from hydroxy, alkoxy, carboxy, alkylcarboxy, amino, nitro, mercapto, halo, keto, sulfoxy, alkyl, mercapto, amide, nitrile, isonitrile, ester and other carbonyl containing groups and R is hydrogen, CHO or an optionally substituted hydrocarbyl group having 1 to 36 carbon atoms.

R may be hydrogen, CHO or an optionally substituted alkyl, alkenyl or aryl group having 1 to 30 carbon atoms, preferably 1 to 20 carbon atoms, more preferably 1 to 10 carbon atoms.

Suitably R may be hydrogen or an optionally substituted alkyl, alkenyl or aryl group having 1 to 30 carbon atoms, preferably 1 to 20 carbon atoms, more preferably 1 to 10 carbon atoms.

In some embodiments R is CHO and the aldehyde is a malondialdehyde derivative.

Preferably R is hydrogen or an optionally substituted alkyl or alkenyl group having 1 to 30, preferably 1 to 20, suitably 1 to 10 carbon atoms.

In some embodiments R is an optionally substituted alkyl or alkenyl group having 1 to 7, preferably 1 to 6 carbon atoms.

In some embodiments R is an optionally substituted alkyl or alkenyl group having 8 to 14, preferably 8 to 12 carbon atoms.

R may be substituted with one or more substituents selected from keto, hydroxyl, halo, carboxy, acyl, nitro, amino, mercapto, alkoxy, sulfoxy, ester, nitrile, isonitrile or amide. The carbon backbone may be interrupted by one or more heteroatoms, for example one or more oxygen, nitrogen or sulfur atoms.

In some preferred embodiments R is an unsubstituted alkyl group having 1 to 8, preferably 1 to 6 carbon atoms.

In some preferred embodiments R is an unsubstituted alkyl group having 4 to 16, preferably 8 to 12 carbon atoms.

R may be selected from hydroxy methylene, methyl, butyl, hexyl, octyl, decyl and dodecyl. These groups may be straight-chained or branched. Preferably they are straight-chained.

Suitably R is selected from hydrogen, hydroxymethylene, methyl, n-butyl and n-hexyl.

R may be selected from methyl, n-butyl, n-hexyl n-octyl, n-decyl and n-dodecyl.

Preferably R is selected from methyl, n-butyl and n-hexyl.

Most preferably R is selected from n-butyl and n-hexyl.

X is selected from hydroxy, alkoxy, carboxy, alkylcarboxy, amino, nitro, mercapto, halo, keto, sulfoxy, alkyl, mercapto, amide, nitrile, isonitrile, ester and other carbonyl containing groups.

In some preferred embodiments X is a group of formula OZ wherein Z is H, $R^1$, $R^3COR^2$, $R^3CONHR^2$, $R^3NHCOR^2$, $R^3OCOR^2$, or $R^3COOR^2$ wherein each of $R^1$ and $R^2$ is an optionally substituted hydrocarbyl group having 1 to 20 carbon atoms, preferably 1 to 8 carbon atoms, preferably 1 to 6 carbon atoms and most preferably 1 to 4 carbon atoms; and $R^3$ is a bond or an alkylene group having 1 to 20 carbon atoms, preferably 1 to 8 carbon atoms, preferably 1 to 6 carbon atoms and most preferably 1 to 4 carbon atoms.

$R^1$ and $R^2$ are optionally substituted alkyl groups. Preferred substituents are hydroxyl groups, especially terminal hydroxyl groups.

Suitably $R^1$ and $R^2$ are alkyl groups, preferably $C_1$ to $C_4$ alkyl groups.

In some especially preferred embodiments Z is H or $R^1$ wherein R' is a $C_1$ to $C_4$ alkyl group or a group of formula $HO(CH_2)_n$ wherein n is 1 to 6, preferably 1 to 4, preferably 2 or 3.

In some preferred embodiments X is a halo group. Suitably X is F, Br or Cl, preferably Br.

In some especially preferred embodiments X is selected from OH, $O(CH_2)_nA$, Cl, Br or F wherein n is from 1 to 6, preferably 1 to 4 and A is H or OH.

In some preferred embodiments X is $HOCH_2CH_2$ and R is hydrogen.

In some preferred embodiments X is Br and R is CHO.

In some most preferred embodiments X is OH and the aldehyde is a 2-hydroxy aldehyde.

In some preferred embodiments X is OH and R is a $C_1$ to $C_6$ alkyl or hydroxyalkyl group.

The compound of formula (II) is an aldehyde which is substituted at the 2 position. It may have one or more further substituents.

Suitable further substituents may be selected from a hydroxyl substituent, a further aldehyde group, a keto group, a carboxy group, an acyl group, a halo group, an alkoxy group, an alkyl group, a nitro group, an amino group, a sulfoxy group, a mercapto group, an amide, an ester, a nitrile group or an isonitrile group.

Preferred halo substituents are chloro, fluoro, and bromo.

Preferred alkoxy substituents are methoxy, ethoxy, propoxy and butoxy, including isomers thereof.

Preferred alkyl substituents are $C_1$ to $C_8$ alkyl, preferably $C_1$ to $C_6$ alkyl, including isomers thereof.

In some embodiments the aldehyde may include a further aldehyde functional group. Such further aldehyde groups may be α-substituted.

In preferred embodiments the aldehyde includes a hydrocarbon chain. This is suitably a chain with a carbon backbone. However compounds in which the carbon backbone is interrupted by one or more heteroatoms are also within the scope of the invention. For example the carbon backbone may be interrupted by one or more oxygen, sulfur or nitrogen molecules and thus the aldehyde may include an ether, a thioether, an amine or a disulfide moiety.

The aldehyde may be predominantly aliphatic or predominantly aromatic in nature. Preferably the aldehyde is aliphatic. However it may include one or more double bonds and/or one or more cyclic groups. It may be straight-chain or branched.

Suitable aldehydes for use herein include 2-hydroxydecanal, 2-hydroxydodecanal, 2-hydroxytetradecanal, 2-hydroxyhexanal, 2-hydroxyoctanal, 2-hydroxypropanal, glyceraldehyde, 2-hydroxybutanal, 3-hydroxybutanal, 4-hydroxybutanal, bromomalonaldehyde, 2-(2-hydroxyethoxy)acetaldehyde, 2-chloro octanal, 2-fluoro octanal, 2-bromo octanal, 6-hydroxyhexanal, 3-hydroxypropanal and 4-hydroxy-but-2-enal.

Suitable alpha-substituted aldehydes for use herein include hydroxydecanal, 2-hydroxydodecanal, 2-hydroxytetradecanal, 2-hydroxyhexanal, 2-hydroxyoctanal, 2-hydroxypropanal, glyceraldehyde, 2-hydroxybutanal, bromomalonaldehyde, 2-(2-hydroxyethoxy)acetaldehyde, 2-chloro octanal, 2-fluoro octanal and 2-bromo octanal.

Suitable alpha-substituted aldehydes for use herein include 2-hydroxyhexanal, 2-hydroxyoctanal, 2-hydroxypropanal, glyceraldehyde, 2-hydroxybutanal, bromomalonaldehyde, 2-(2-hydroxyethoxy)acetaldehyde, 2-chloro octanal, 2-fluoro octanal and 2-bromo octanal. Suitable hydroxy-substituted aldehydes for use herein include-hydroxydecanal, 2-hydroxydodecanal, 2-hydroxytetradecanal, 2-hydroxyhexanal, 2-hydroxyoctanal, 2-hydroxypropanal, glyceraldehyde, 6-hydroxyhexanal, 3-hydroxypropanal, 4-hydroxy-but-2-enal, 2-hydroxybutanal, 3-hydroxybutanal and 4-hydroxybutanal.

Preferred hydroxy-substituted aldehydes for use herein include 2-hydroxyhexanal, 2-hydroxyoctanal, 2-hydroxypropanal, glyceraldehyde, 6-hydroxyhexanal, 3-hydroxypropanal, 4-hydroxy-but-2-enal, 2-hydroxybutanal, 3-hydroxybutanal and 4-hydroxybutanal.

Preferred alpha-hydroxy substituted aldehydes for use herein include 2-hydroxyhexanal, 2-hydroxyoctanal, 2-hydroxypropanal, glyceraldehyde, 2-hydroxybutanal, 3-hydroxybutanal, 4-hydroxybutanal, bromomalonaldehyde and 2-(2-hydroxyethoxy)acetaldehyde.

More preferred aldehydes for use herein include 2-hydroxyhexanal, 2-hydroxyoctanal, 2-hydroxypropanal and glyceraldehyde.

Most preferred hydroxy-substituted aldehydes for use herein are 2-hydroxyhexanal and 2-hydroxyoctanal and 2-hydroxypropanal.

Suitably the composition comprises an aldehyde in the amount of at least 0.1 wt %, suitably at least 0.5 wt %, preferably at least 1 wt %, for example at least 1.5 wt %.

The composition may comprise an aldehyde in the amount of up to 50 wt %, preferably up to 30 wt %, suitably up to 20 wt %, preferably up to 10 wt %, more preferably up to 5 wt %, for example up to 4 wt %, up to 3 wt % or up to 2.75 wt %.

In some embodiments the composition comprises from 0.1 to 10 wt % of an aldehyde, preferably from 0.5 to 5 wt %, suitably from 0.5 to 3 wt %.

In some alternative embodiments the composition may comprise much greater concentrations of aldehyde, for example from 20 to 100 wt %, preferably from 50 to 100 wt %, for example from 70 to 100 wt % or from 90 to 100 wt %.

The composition of the second aspect may comprise a mixture of two or more aldehydes.

In such embodiments the above amounts refer to the total amount of all such compounds present in the composition.

In some embodiments the composition of the second aspect comprises a mixture of two or more aldehydes.

In some embodiments the composition of the second aspect comprises 2-hydroxyoctanal and one or more further aldehydes.

In some embodiments the composition of the second aspect comprises glyceraldehyde and one or more further aldehydes.

In some embodiments the composition of the second aspect comprises 2-hydroxyoctanal and glyceraldehyde. It may optionally comprise one or more further aldehydes.

In some embodiments the composition of the second aspect comprises a first aldehyde having less than 10 carbon atoms and a second aldehyde having 10 or more carbon atoms. It may optionally comprise one or more further aldehydes. For example the composition of the second aspect may comprises a first alpha-substituted aldehyde having 3 to 9 carbon atoms, preferably 3 to 8 carbon atoms and a second aldehyde having 10 to 18 carbon atoms, preferably 10 to 16 carbon atoms, more preferably 10 to 14 carbon atoms. It may optionally comprise one or more further aldehydes.

In some embodiments the composition of the second aspect comprises one or more aldehydes selected from 2-hydroxydecanal, 2-hydroxydodecanal and 2-hydroxytetradecanal and one or more further aldehydes selected from 2-hydroxyhexanal, 2-hydroxyoctanal, 2-hydroxypropanal, glyceraldehyde, 2-hydroxybutanal, 3-hydroxybutanal, 4-hydroxybutanal, bromomalonaldehyde, 2-(2-hydroxyethoxy) acetaldehyde, 2-chloro octanal, 2-fluoro octanal, 2-bromo octanal, 6-hydroxyhexanal, 3-hydroxypropanal and 4-hydroxy-but-2-enal.

In some embodiments the composition of the second aspect may comprise one or aldehydes selected from 2-hydroxydecanal, 2-hydroxydodecanal and 2-hydroxytetradecanal and one or more further aldehydes selected from 2-hydroxyhexanal, 2-hydroxyoctanal, 2-hydroxypropanal and glyceraldehyde.

The compositions used in the present invention may comprise a succinimidyl ester.

Suitable succinimidyl esters include the compounds described in FR2937543.

Preferred succinimidyl esters include esters of monocarboxylic acids and esters of dicarboxylic acids.

Suitable succinimidyl esters of dicarboxylic acids include compounds of formula (III):

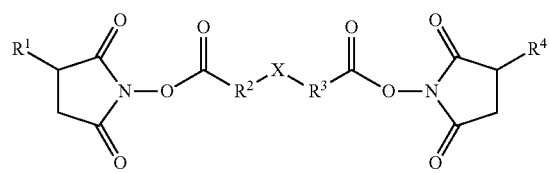

(III)

wherein each of $R^1$ and $R^4$ is independently hydrogen or a sulfonate moiety; each of $R^2$ and $R^3$ is independently a bond or an optionally substituted alkylene, alkenylene or arylene group and X is selected from a bond, $(CH_2)_n$, O, S or S—S.

$R^1$ is hydrogen or a sulfonate moiety. By sulfonate moiety we mean to refer to a group of formula $SO_3X$ where X is hydrogen, an alkali metal or ammonium ion. Preferably $R^1$ is hydrogen.

$R^4$ is hydrogen or a sulfonate moiety. By sulfonate moiety we mean to refer to a group of formula $SO_3X$ where X is hydrogen, an alkali metal or ammonium ion. Preferably $R^4$ is hydrogen.

$R^2$ is a bond or an optionally substituted alkylene, alkenylene or arylene group. It may be substituted with one or more substituents selected from keto, hydroxyl, halo, carboxy, acyl, nitro, amino, mercapto, alkoxy, sulfoxy, ester, nitrile, isonitrile or amide.

Preferably $R^2$ is an optionally substituted alkylene group. More preferably $R^2$ is an unsubstituted alkylene group.

$R^2$ may be straight chain or branched. Preferably $R^2$ has 1 to 12, more preferably 1 to 18, suitably 1 to 6, preferably 1 to 4, for example 1 or 2 carbon atoms.

$R^3$ is a bond or an optionally substituted alkylene, alkenylene or arylene group. It may be substituted with one or more substituents selected from keto, hydroxyl, halo, carboxy, acyl, nitro, amino, mercapto, alkoxy, sulfoxy, ester, nitrile, isonitrile or amide.

Preferably $R^3$ is an optionally substituted alkylene group. More preferably $R^3$ is an unsubstituted alkylene group.

$R^3$ may be straight chain or branched. Preferably $R^3$ has 1 to 12, more preferably 1 to 18, suitably 1 to 6, preferably 1 to 4, for example 1 or 2 carbon atoms.

X is a selected from a bond, $(CH_2)_n$, O, S or S—S. n is preferably from 1 to 10, for example from 1 to 4.

Preferably X is selected from S and S—S.

Some preferred diesters for use herein include the following compounds:

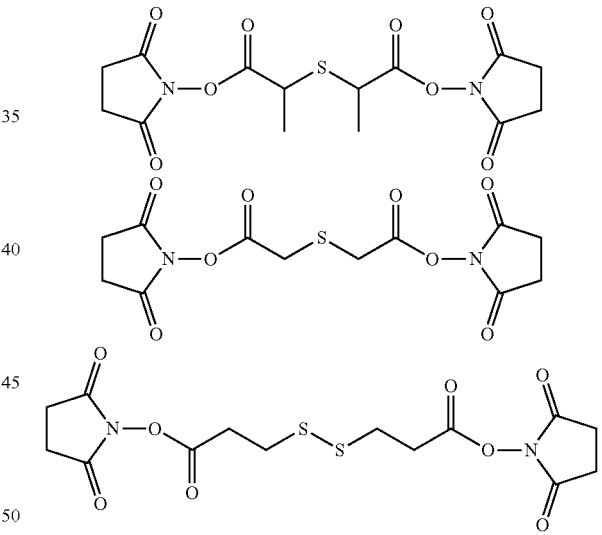

Preferred succinimidyl esters for use herein are esters of monocarboxylic acids.

Especially preferred succinimidyl esters for use herein include compounds of formula (IV):

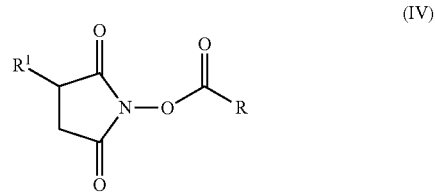

(IV)

wherein R is optionally substituted hydrocarbyl group having at least 5 carbon atoms; and R¹ is hydrogen or a solubilising agent.

R¹ is hydrogen or a solubilising group.

The solubilising group may be selected from any moiety which improves the water solubility of the compound of formula (I). Suitable solubilising group include hydroxy, alkoxy, polyalkoxy, alkylcarboxy, sulfo and phosphono groups.

Preferably R' is selected from hydrogen and a sulfonate moiety.

In some embodiments R¹ is a sulfonate moiety. By sulfonate moiety we mean to refer to a group of formula $SO_3X$ where X is hydrogen, an alkali metal or ammonium ion.

Preferably R¹ is hydrogen.

Preferably R is an optionally substituted hydrocarbyl group having up to 36 carbon atoms, suitably up to 30 carbon atoms, preferably up to 24 carbon atoms, more preferably up to 20 carbon atoms, preferably up to 18 carbon atoms, more preferably up to 14 carbon atoms and most preferably up to 12 carbon atoms.

R may be an optionally substituted alkyl, alkenyl, aryl, alkaryl or aralkyl group having 5 to 36 carbon atoms, suitably up to 5 to 30 carbon atoms, preferably 5 to 20 carbon atoms, more preferably 5 to 12 carbon atoms.

In some embodiments R is an aryl group having 6 to 24, preferably 6 to 16, more preferably 6 to 10 carbon atoms.

In some embodiments R is an optionally substituted phenyl group. R may be phenyl.

In some embodiments R is an optionally substituted alkyl or alkenyl group having 5 to 24, preferably 5 to 16, suitably 6 to 10 carbon atoms.

R may be substituted with one or more substituents selected from keto, hydroxyl, halo, aryl, carboxy, acyl, nitro, amino, mercapto, alkoxy, sulfoxy, ester, nitrile, isonitrile or amide. The carbon backbone may be interrupted by one or more heteroatoms, for example one or more oxygen, nitrogen or sulfur atoms.

In some preferred embodiments R is an unsubstituted alkyl group having 5 to 11, preferably 6 to 10, more preferably 7 to 9 carbon atoms.

Suitably R is selected from n-heptyl and n-nonyl.

Preferably R is n-heptyl.

Suitably the composition comprises a succinimidyl ester in an amount of at least 0.1 wt %, suitably at least 0.5 wt %, preferably at least 1 wt %, for example at least 1.5 wt %.

The composition may comprise a succinimidyl ester in an amount of up to 50 wt %, preferably up to 30 wt %, suitably 20 wt %, for example up to 10 wt %, for example up to 5 wt %, up to 3 wt % or up to 2.75 wt %.

In some embodiments the composition may suitably comprise from 0.1 to 10 wt %, preferably 0.5 to 5 wt %, for example 1 to 3 wt % of a succinimidyl ester.

The composition of the second aspect may comprise two or more succinimidyl esters. In such embodiments the above amounts refer to the total amount of all such compounds present in the composition.

The compositions used in the present invention further comprise a chelating agent and/or a salt of an amine and a carboxylic acid.

For the avoidance of doubt by this we mean that the composition may contain one or more than one chelating agent and no salts of an amine and a carboxylic acid; no chelating agents and one or more than one salts of an amine and a carboxylic acid; or one or more chelating agents and one or more salts of an amine and a carboxylic acid.

Any suitable chelating agent may be used. Compounds of this type will be known to those skilled in the art.

Preferred chelating agents for use herein are polycarboxylic acid derived chelating agents.

The composition used in the present invention comprises a chelating agent. In some preferred embodiments the chelating agent is selected from glutamic acid N,N-diacetic acid (GLDA), diethylene triamine pentaacetic acid (DTPA), imido disuccinic acid (IDS), L-aspartic acid diacetic acid (ASDA), ethylene diamine tetraacetic acid (EDTA), ethylene diamine disuccinic acid (EDDS), hydroxyethyl ethylenediaminetriacetic acid (HEDTA), citric acid and mixtures thereof.

The chelating agents used in the present invention are derivatives of polycarboxylic acids. By this we mean that the chelating agent includes two or more carboxylic acid moieties or salts thereof. Suitably chelating agents for use therein may include 3, 4 or 5 carboxylic acid moieties.

Glutamic acid N,N-diacetic acid (GLDA) has the structure shown in formula V:

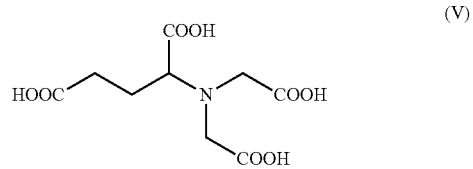 [SMILES: O=C(O)CCC(C(=O)O)N(CC(=O)O)CC(=O)O]

(V)

In the compositions of the present invention GLDA, may be present having the structure shown in formula V and/or the same structure in which a number of the acidic protons have been replaced, i.e. in which 1, 2, 3 or 4 of the acid groups have been neutralised or partially neutralised. It may be present as a free acid or a salt or complex thereof.

GLDA may be present as either enantiomer or a mixture thereof. Preferably at least 50% is present as [S]-GLDA, preferably at least 70%, more preferably at least 90%, most preferably at least 95 wt %, for example about 98 wt %. In some preferred embodiments the GLDA consists essentially of the S enantiomer.

GLDA is commercially available as a solution comprising 38 wt % of the tetrasodium salt and is sold under the trade mark Dissolvine GL-38.

Diethylene triamine pentaacetic acid (DTPA) has the structure shown in formula VI:

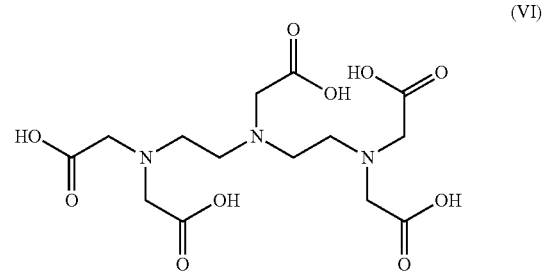 [SMILES: O=C(O)CN(CCN(CC(=O)O)CC(=O)O)CCN(CC(=O)O)CC(=O)O]

(VI)

When component (b) comprises DTPA, this may be provided in a form having the structure shown in formula VI or in a form having the same structure in which a number of the hydrogen atoms have been replaced. Thus component (b) may comprise salts in which 1, 2, 3, 4 or 5 of the acid groups have been neutralised or partially neutralised.

When a salt of DTPA is included, this may be the salt of an alkali metal, an alkaline earth metal, ammonia or a suitable amine.

When a monovalent counterion is used the salt may be the monosalt, the disalt, the trisalt, the tetra salt or the pentasalt. For a divalent cation the monosalt or disalt may be present. Mixed salts may also exist, for example, the disodium magnesium salt or the sodium magnesium salt may be present. Preferably the counterion(s) to the DTPA residue is/are selected from one or more of sodium, magnesium, calcium, potassium, lithium, ammonium, and a quaternary ammonium ion.

Preferably DTPA when present is included as the pentasodium salt.

Iminodisuccinic acid (IDS) has the structure shown in formula VII:

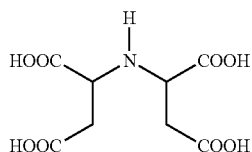

(VII)

In the compositions of the present invention IDS may be present having the structure shown in formula VII and/or the same structure in which a number of the acidic protons have been replaced, i.e. in which 1, 2, 3 or 4 of the acid groups have been neutralised or partially neutralised. It may be present as a free acid or a salt or complex thereof.

IDS or a salt thereof may be present as either enantiomer or a mixture thereof. Preferably it is present as a racemic mixture.

IDS is commercially available as a solution comprising 34 wt % of the tetrasodium salt and is sold under the trade mark Baypure CX100.

L-aspartic acid diacetic acid (ASDA) is a structural isomer of IDS and has the structure shown in formula VIII:

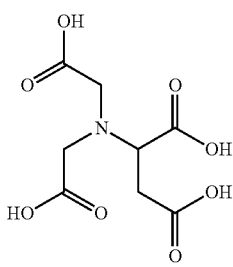

(VIII)

In the compositions of the present invention ASDA may be present having the structure shown in formula VIII and/or the same structure in which a number of the acidic protons have been replaced, i.e. in which 1, 2, 3 or 4 of the acid groups have been neutralised or partially neutralised. It may be present as a free acid or a salt or complex thereof.

EDTA has the structure shown in formula IX:

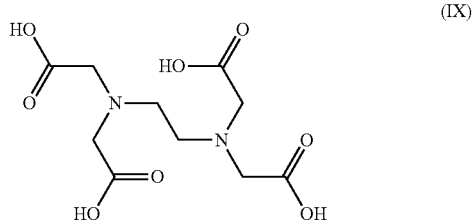 [SMILES: O=C(O)CN(CCN(CC(=O)O)CC(=O)O)CC(=O)O]

(IX)

When component (b) comprises EDTA, this may be provided in a form having the structure shown in formula IX or in a form having the same structure in which a number of the hydrogen atoms have been replaced. Thus component (b) may comprise salts in which 1, 2, 3 or 4 of the acid groups have been neutralised or partially neutralised.

When a salt of EDTA is included, this may be the salt of an alkali metal, an alkaline earth metal, ammonia or a suitable amine.

When a monovalent counterion is used the salt may be the monosalt, the disalt, the trisalt or the tetrasalt. For a divalent cation the monosalt or disalt may be present. Mixed salts may also exist, for example, the disodium magnesium salt or the sodium magnesium salt may be present. Preferably the counterion(s) to the EDTA residue is/are selected from one or more of sodium, magnesium, calcium, potassium, lithium, ammonium, and a quaternary ammonium ion.

Preferably EDTA when present is present as the tetrasodium salt.

Ethylenediamine disuccinic acid (EDDS) which has the structure shown in formula X:

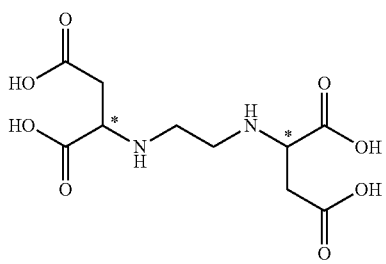

(X)

EDDS includes two stereogenic centres and there are three possible stereoisomers. A particularly preferred configuration is [S,S]-ethylenediamine disuccinic acid which is readily biodegradable.

In the compositions of the present invention "EDDS" may be present having the structure shown in formula X and/or the same structure in which a number of the hydrogen atoms have been replaced. Thus EDDS may also contain succinate salts in which 1, 2, 3 or 4 of the acid groups have been neutralised or partially neutralised. It may be present as a free acid or a salt or complex thereof.

One commercially available material is trisodium ethylenediamine disuccinate. The commercial product (Natrlquest E30 (RTM)) is supplied as an aqueous solution comprising 30% by weight EDDS (expressed as free acid), or 37 wt % of the trisodium salt (including the counterion).

Another commercially available form of EDDS is the tetra acid, sold under the trade mark Natrlquest E80. This is provided as a powder which contains 80 wt % solid [S,S] EDDS as an acid, and water of crystallisation.

Hydroxyethylethylenediaminetriacetic acid (known as HEEDTA or HEDTA) has the structure shown in formula XI:

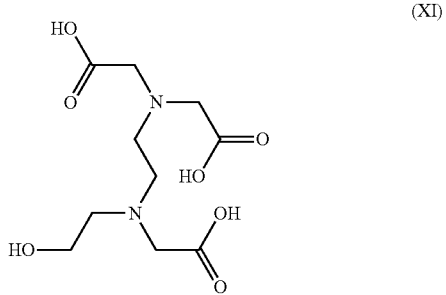 [SMILES: O=C(O)CN(CCO)CCN(CC(=O)O)CC(=O)O]

(XI)

In the compositions of the present invention HEDTA may be present having the structure shown in formula XI and/or the same structure in which a number of the acidic protons have been replaced, i.e. in which 1, 2 or 3 of the acid groups have been neutralised or partially neutralised. It may be present as a free acid or a salt or complex thereof.

HEDTA is commercially available from Akzo Nobel as the trisodium salt under the trade mark Dissolvine H40.

Citric acid may be included as the free acid or as an alkali metal or ammonium salt.

In some preferred embodiments the chelating agent is selected from DTPA, GLDA, IDS and mixtures thereof.

In some especially preferred embodiments the chelating agent is selected from DTPA, GLDA and mixtures thereof.

In some embodiments the composition comprises a polycarboxylic acid derived chelating agent in an amount of at least 0.1 wt %, suitably at least 1 wt %, preferably at least 3 wt %, for example at least 5 wt %, at least 6 wt %, at least 7 wt %, or at least 8 wt %.

The composition may comprise a polycarboxylic acid derived chelating agent in an amount of up to 50 wt %, preferably up to 40 wt %, suitably up to 30 wt %, for example up to 20 wt %, up to 15 wt % or up to 12 wt %.

In some embodiments the composition may comprise the carboxylic acid derived chelating agent in an amount of from 0.1 to 15 wt %, suitably 0.25 to 10 wt %, preferably 0.5 to 5 wt %, for example from 1 to 3 wt %.

The composition may comprise a mixture of polycarboxylic acid derived chelating agents. In such embodiments the above amounts refer to the total amount of all such chelating agents present in the composition.

In some embodiments the composition comprises GLDA. In some embodiments the composition comprises DTPA. In some embodiments the composition comprises a mixture of GLDA and DTPA. In such embodiments the ratio of GLDA to DTPA is preferably from 1:10 to 10:1, preferably from 1:5 to 5:1, for example from 1:2 to 2:1.

The compositions of the present invention may comprise an amine salt of a carboxylic acid.

Suitable carboxylic acids include monocarboxylic acids, dicarboxylic acids and polycarboxylic acids.

Monocarboxylic acids are preferred.

In preferred embodiments the carboxylic acid includes a hydrocarbon chain. This is suitably a chain with a carbon backbone. However compounds in which the carbon backbone is interrupted by one or more heteroatoms are also within the scope of the invention. For example the carbon backbone may be interrupted by one or more oxygen, sulphur or nitrogen molecules and thus the carboxylic acid may include an ether, a thioether, an amine or a disulfide moiety.

The carboxylic acid may be predominantly aliphatic or predominantly aromatic in nature. Preferably the carboxylic acid is aliphatic. However it may include one or more double bonds and/or one or more cyclic groups. It may be straight-chain or branched.

In some especially preferred embodiments the salt is of a carboxylic acid of formula RCOOH, wherein R is an optionally substituted hydrocarbyl group, suitably an optionally substituted alkyl, alkenyl or aryl group.

In some embodiments R may have up to 40 carbon atoms, preferably up to 30 carbon atoms, more preferably up to 24 carbon atoms, suitably up to 18 carbon atoms, for example up to 12 carbon atoms.

In preferred embodiments the composition comprises a salt of an amine and a carboxylic acid having 4 to 10 carbon atoms.

Some preferred carboxylic acids have from 5 to 9 carbon atoms, for example 6 to 8 carbon atoms.

R may be an optionally substituted alkyl, alkenyl or aryl group having 3 to 9 carbon atoms, preferably 4 to 8 carbon atoms, more preferably 5 to 7 carbon atoms.

Preferably R is an optionally substituted alkyl or alkenyl group having 3 to 9, preferably 4 to 8, suitably 5 to 7 carbon atoms.

R may be substituted with one or more substituents selected from keto, hydroxyl, halo, carboxy, acyl, nitro, amino, mercapto, alkoxy, sulfoxy, ester, nitrile, isonitrile or amide. The carbon backbone may be interrupted by one or more heteroatoms, for example one or more oxygen, nitrogen or sulfur atoms.

Preferably R is a straight chain alkyl group.

In some preferred embodiments R is an unsubstituted alkyl group having 3 to 9, preferably 4 to 8, more preferably 5 to 7 carbon atoms.

Suitably R is selected from propyl, butyl, pentyl, hexyl, heptyl, cetyl, nonyl, including isomers and mixtures thereof.

Preferably R is selected from n-pentyl and n-heptyl.

Most preferably R is n-heptyl.

The present invention relates to the salt of a carboxylic acid and an amine.

Any suitable amine may be used to form the salt. Suitable amines include primary, secondary and tertiary amines, and ammonia.

In some preferred embodiments the amine is an alkylamino and/or hydroxyalkyl amino compound of formula $R^1R^2R^3N$, wherein each of $R^1$, $R^2$ and $R^3$ is hydrogen or an alkyl group or a hydroxyalkyl group. Each of $R^1$, $R^2$ and $R^3$ may be the same or different. Suitably each of $R^1$, $R^2$ and $R^3$ is independently selected from hydrogen and an alkyl or hydroxyalkyl group having 1 to 6 carbon atoms, for example 1 to 4 carbon atoms. Each of $R^1$, $R^2$ and $R^3$ may be independently selected from hydrogen, methyl, ethyl, propyl, butyl, pentyl, hexyl, hydroxymethyl, hydroxyethyl, hydroxypropyl, hydroxybutyl, hydroxypentyl, hydroxyhexyl and isomers thereof. The amine may be an alkylamine, a hydroxyalkylamine, a dialkylamine, a hydroxyalkyl alkyl amine, a dihydroxyalkylamine, a trialkylamine, a dialkylhydroxyalkylamine, a dihydroxyalkylamine or a trihydroxyalkylamine. There are many different compounds of this type and these will be known to the person skilled in the art. In some embodiments the amine is a cyclic amine.

In some embodiments the amine is a primary amine. Suitable primary amines include methylamine, ethylamine, propylamine, butylamine, pentylamine, hexylamine, 2-aminobutanol, ethanolamine, cyclohexylamine, aminopropanediol, isopropanolamine, mixed isopropanolamines, tromethamine and benzylamine.

Preferably the amine is a secondary amine or a tertiary amine.

Suitable secondary amine compounds for use herein include dimethylamine, N,N-methylethylamine, N,N-methylpropylamine, N,N-methylbutylamine, diethylamine, N,N-ethylpropylamine, N,N-ethylbutylamine, dipropylamine, N,N-propylbutylamine, dibutylamine, N,N-butylmethylamine, N,N-butylethylamine, N,N-butylpropylamine, N,N-methylmethanolamine, N,N-methylethanolamine, diethanolamine, N,N-methylpropanolamine, dipropanolamine, N,N-methylbutanolamine, dibutanolamine, N,N-ethylmethanolamine, N,N-ethylethanolamine, N,N-ethylpropanolamine, N,N-ethylbutanolamine, N,N-propylmethanolamine, N,N-propylethanolamine, N,N-propylpropanolamine, N,N-propylbutanolamine, N,N-butylmethanolamine, N,N-butylethanolamine, N,N-butylpropanolamine, N,N-butylbutanolamine, 2-(2-aminoethoxy)ethanol, aminoethyl propanediol, aminomethyl propanediol, aminoethyl propanol, diisopropylamine, diisopropanolamine, morpholine and mixtures and isomers thereof.

Some preferred tertiary amine compounds for use herein include trimethylamine, N,N-dimethylethylamine, N,N-dimethylpropylamine, N,N-dimethylbutylamine, triethylamine, N,N-diethylmethylamine, N,N-diethylpropylamine, N,N-diethylbutylamine, tripropylamine, N,N-dipropylmethylamine, N,N-dipropylethylamine, N,N-dipropylbutylamine, tributylamine, N,N-dibutylmethylamine, N, N-dibutylethylamine, N,N-dibutylpropylamine, N,N-dimethylmethanolamine, methyldimethanolamine, N,N-dimethylethanolamine, methyldiethanolamine, N,N-dimethylpropanolamine, methyldipropanolamine, N,N-dimethylbutanolamine, methyldibutanolamine, N,N-diethylmethanolamine, ethyldimethanolamine, N,N-diethylethanolamine, ethyldiethanolamine, N,N-diethylpropanolamine, ethyldipropanolamine, N,N-diethylbutanolamine, ethyldibutanolamine, N,N-dipropylmethanolamine, propyldimethanolamine, N,N-dipropylethanolamine, propyldiethanolamine, N,N-dipropylpropanolamine, propyldipropanolamine, N,N-dipropylbutanolamine, propyldibutanolamine, N,N-dibutylmethanolamine, butyldimethanolamine, N,N-dibutylethanolamine, butyldiethanolamine, N,N-dibutylpropanolamine, butyldipropanolamine, N,N-dibutylbutanolamine, butyldibutanolamine, trimethanolamine, triethanolamine, tripropanolamine, tributanolamine, diethylhexylamine, dimethyltolylamine, bis-hydroxyethyl tromethamine, diethylethanolamine, dimethylamino methylpropanol, dimethyl isopropanolamine, dimethyl MEA, hydroxyethyl methyl tolyl amine, triisopropanolamine, bis-tris (2-[Bis(2-hydroxyethyl)amino]-2-(hydroxymethyl)propane-1,3-diol) and mixtures and isomers thereof.

In some embodiments the amine may be a diamine, a triamine or a polyamine, having two three or more nitrogen atoms. However preferred amines are monoamines or diamines, especially monoamines. When the amine is a diamine the salt may be a monosalt in which there is only one mole of acid per amine or a disalt in which there are two moles of acid per amine.

Suitable polyamines include polyalkylene polyamines.

Preferred diamines are optionally substituted alkylene diamines, for example ethylene diamines. Thus the amine may be an ethylene diamine of formula $R^1R^2NCH_2CH_2NR^3R^4$ wherein each of each of $R^1$, $R^2$, $R^3$ and $R^4$ is hydrogen or an alkyl group or a hydroxyalkyl group. Each of $R^1$, $R^2$, $R^3$ and $R^4$ may be the same or different. Suitably each $R^1$, $R^2$, $R^3$ and $R^4$ is independently selected from hydrogen and an alkyl or hydroxyalkyl group having 1 to 6 carbon atoms, for example 1 to 4 carbon atoms. Each of $R^1$, $R^2$, $R^3$ and $R^4$ may be independently selected from hydrogen, methyl, ethyl, propyl, butyl, pentyl, hexyl, hydroxymethyl, hydroxyethyl, hydroxypropyl, hydroxybutyl, hydroxypentyl and hydroxyhexyl.

Some especially preferred salts for use herein include the compounds having the following structures.

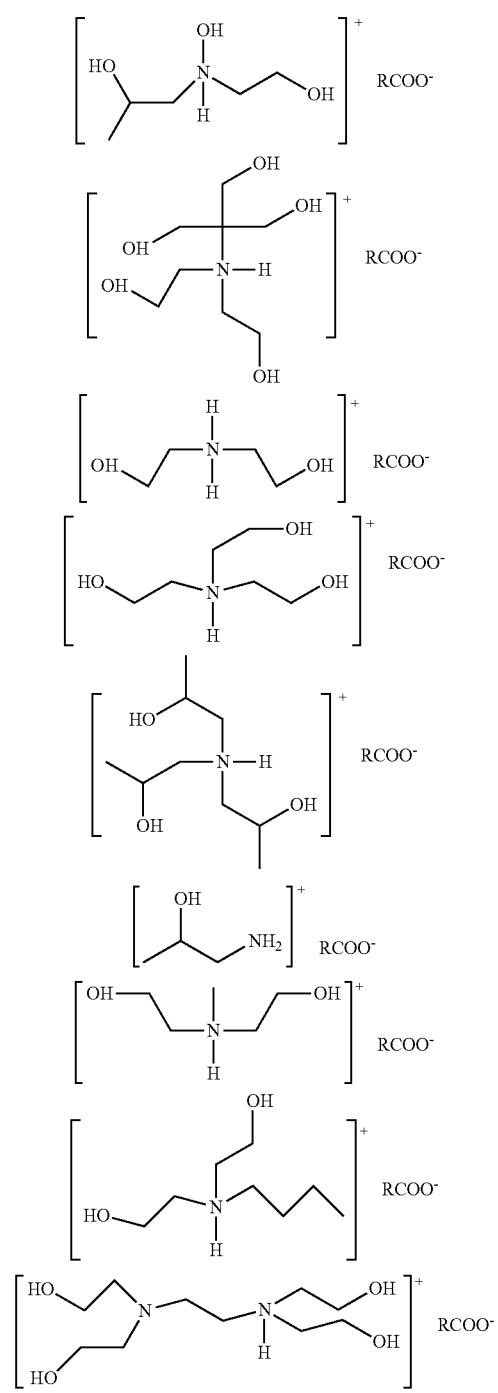

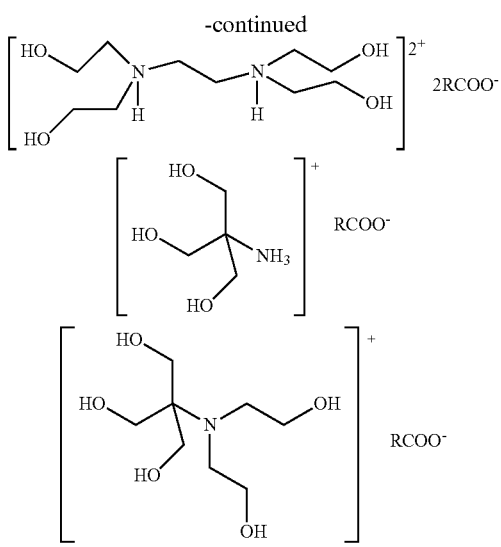

wherein R is an alkyl or alkenyl group having 3 to 9 carbon atoms, preferably pentyl or heptyl.

In especially preferred embodiments the composition of the present invention includes a salt of octanoic acid and an amine selected from triethanolamine and diethanolamine, preferably triethanolamine.

Suitably the composition comprises an amine salt of a carboxylic acid wherein the carboxylic acid has 4 to 10 carbon atoms in the amount of at least 0.1 wt %, suitably at least 0.5 wt %, preferably at least 1 wt %, for example at least 1.5 wt %.

The composition may comprise an amine salt of a carboxylic acid wherein the carboxylic acid has 4 to 10 carbon atoms in an amount of up to 50 wt %, preferably up to 30 wt %, suitably up to 20 wt %, preferably up to 10 wt %, more preferably up to 5 wt %, for example up to 4 wt %, up to 3 wt % or up to 2.75 wt %.

In some embodiments the composition comprises from 0.1 to 10 wt % of the amine salt of a carboxylic acid wherein the carboxylic acid has 4 to 10 carbon atoms, preferably from 0.5 to 5 wt %, suitably from 0.5 to 3 wt %.

In some alternative embodiments the composition may comprise much greater concentrations of an amine salt of a carboxylic acid wherein the carboxylic acid has 4 to 10 carbon atoms, for example from 20 to 100 wt %, preferably from 50 to 100 wt %, for example from 70 to 100 wt % or from 90 to 100 wt %.

The composition of the second aspect may comprise a mixture of two or more amine salts of a carboxylic acid wherein the carboxylic acid has 4 to 10 carbon atoms. In such embodiments the above amounts refer to the total amount of all such compounds present in the composition.

In some preferred embodiments the method of the first aspect involves contacting the material with an aldehyde, preferably an alpha-substituted aldehyde and/or a hydroxy-substituted aldehyde.

In some preferred embodiments the composition of the second aspect comprises an aldehyde, preferably an alpha-substituted aldehyde and/or a hydroxysubstituted aldehyde.

In some preferred embodiments the method of the first aspect involves contacting the material with a succinimidyl ester, preferably a compound of formula (IV).

In some preferred embodiments the composition of the second aspect comprises a succinimidyl ester, preferably a compound of formula (IV).

In some preferred embodiments the method of the first aspect involves contacting the material with a chelating agent, preferably a polycarboxylic acid derived chelating agent.

In some preferred embodiments the composition of the second aspect comprises a chelating agent, preferably a polycarboxylic acid derived chelating agent.

In some preferred embodiments the method of the first aspect involves contacting the material with an amine salt of a carboxylic acid, preferably wherein the carboxylic acid has 4 to 10 carbon atoms.

In some preferred embodiments the composition of the second aspect comprises an amine salt of a carboxylic acid, preferably wherein the carboxylic acid has 4 to 10 carbon atoms.

In some embodiments the method of the first aspect involves contacting the material with an aldehyde, preferably an alpha-substituted aldehyde and/or a hydroxysubstituted aldehyde and a chelating agent, preferably a polycarboxylic acid derived chelating agent.

In some embodiments the composition of the second aspect comprises an aldehyde, preferably an alpha-substituted aldehyde and/or a hydroxysubstituted aldehyde and a chelating agent, preferably a polycarboxylic acid derived chelating agent.

In some embodiments the method of the first aspect involves contacting the material with a succinimidyl ester, preferably a compound of formula (IV) and a chelating agent, preferably a polycarboxylic acid derived chelating agent.

In some embodiments the composition of the second aspect comprises a succinimidyl ester, preferably a compound of formula (IV) and a chelating agent, preferably a polycarboxylic acid derived chelating agent.

In some embodiments the method of the first aspect involves contacting the material with an aldehyde, preferably an alpha-substituted aldehyde and/or a hydroxysubstituted aldehyde and an amine salt of a carboxylic acid, preferably wherein the carboxylic acid has 4 to 10 carbon atoms.

In some embodiments the composition of the second aspect comprises an aldehyde, preferably an alpha-substituted aldehyde and/or a hydroxysubstituted aldehyde and an amine salt of a carboxylic acid, preferably wherein the carboxylic acid has 4 to 10 carbon atoms.

In some embodiments the method of the first aspect involves contacting the material with a succinimidyl ester, preferably a compound of formula (IV) and an amine salt of a carboxylic acid, preferably wherein the carboxylic acid has 4 to 10 carbon atoms.

In some embodiments the composition of the second aspect comprises a succinimidyl ester, preferably a compound of formula (IV) and an amine salt of a carboxylic acid, preferably wherein the carboxylic acid has 4 to 10 carbon atoms.

In some preferred embodiments the method of the first aspect involves contacting the material with:
  a succinimidyl ester, preferably a compound of formula (IV);
  a chelating agent, preferably a polycarboxylic acid derived chelating agent; and
  an amine salt of a carboxylic acid, preferably wherein the carboxylic acid has 4 to 10 carbon atoms.

In some embodiments the composition of the second aspect comprises:
  a succinimidyl ester, preferably a compound of formula (IV);

a chelating agent, preferably a polycarboxylic acid derived chelating agent; and an amine salt of a carboxylic acid, preferably wherein the carboxylic acid has 4 to 10 carbon atoms.

In some preferred embodiments the method of the first aspect involves contacting the material with:

an aldehyde, preferably an alpha-substituted aldehyde and/or a hydroxysubstituted aldehyde;

a chelating agent, preferably a polycarboxylic acid derived chelating agent; and an amine salt of a carboxylic acid, preferably wherein the carboxylic acid has 4 to 10 carbon atoms.

In some embodiments the composition of the second aspect comprises:

an aldehyde, preferably an alpha-substituted aldehyde and/or a hydroxysubstituted aldehyde;

a chelating agent, preferably a polycarboxylic acid derived chelating agent; and an amine salt of a carboxylic acid, preferably wherein the carboxylic acid has 4 to 10 carbon atoms.

In some preferred embodiments the method of the first aspect involves contacting the material with:

an aldehyde selected from 2-hydroxyhexanal, 2-hydroxyoctanal, 2-hydroxypropanal, glyceraldehyde, 2-hydroxybutanal, 3-hydroxybutanal, 4-hydroxybutanal, bromomalonaldehyde and 2-(2-hydroxyethoxy)acetaldehyde; and a chelating agent selected from glutamic acid N,N-diacetic acid (GLDA), diethylene triamine pentaacetic acid (DTPA), imido disuccinic acid (IDS), L-aspartic acid diacetic acid (ASDA), ethylene diamine tetraacetic acid (EDTA), ethylene diamine disuccinic acid (EDDS), hydroxyethyl ethylenediaminetriacetic acid (HEDTA), citric acid and mixtures thereof.

In some preferred embodiments the composition of the second aspect comprises:

an aldehyde selected from 2-hydroxyhexanal, 2-hydroxyoctanal, 2-hydroxypropanal, glyceraldehyde, 2-hydroxybutanal, 3-hydroxybutanal, 4-hydroxybutanal, bromomalonaldehyde and 2-(2-hydroxyethoxy)acetaldehyde; and a chelating agent selected from glutamic acid N,N-diacetic acid (GLDA), diethylene triamine pentaacetic acid (DTPA), imido disuccinic acid (IDS), L-aspartic acid diacetic acid (ASDA), ethylene diamine tetraacetic acid (EDTA), ethylene diamine disuccinic acid (EDDS), hydroxyethyl ethylenediaminetriacetic acid (HEDTA), citric acid and mixtures thereof.

In some preferred embodiments the method of the first aspect involves contacting the material with:

an aldehyde selected from 2-hydroxyhexanal, 2-hydroxyoctanal, 2-hydroxypropanal, glyceraldehyde, 2-hydroxybutanal, 3-hydroxybutanal, 4-hydroxybutanal, bromomalonaldehyde and 2-(2-hydroxyethoxy)acetaldehyde; and an amine salt of a carboxylic acid wherein the carboxylic acid has 4 to 10 carbon atoms and the amine is compound of formula $R^1R^2R^3N$, wherein each of $R^1$, $R^2$ and $R^3$ is independently selected from hydrogen and an alkyl or hydroxyalkyl group having 1 to 6 carbon atoms, for example 1 to 4 carbon atoms.

In some preferred embodiments the composition of the second aspect comprises:

an aldehyde selected from 2-hydroxyhexanal, 2-hydroxyoctanal, 2-hydroxypropanal, glyceraldehyde, 2-hydroxybutanal, 3-hydroxybutanal, 4-hydroxybutanal, bromomalonaldehyde and 2-(2-hydroxyethoxy)acetaldehyde; and an amine salt of a carboxylic acid wherein the carboxylic acid has 4 to 10 carbon atoms and the amine is compound of formula $R^1R^2R^3N$, wherein each of $R^1$, $R^2$ and $R^3$ is independently selected from hydrogen and an alkyl or hydroxyalkyl group having 1 to 6 carbon atoms, for example 1 to 4 carbon atoms.

In some preferred embodiments the method of the first aspect involves contacting the material with:

an aldehyde selected from 2-hydroxyhexanal, 2-hydroxyoctanal, 2-hydroxypropanal, glyceraldehyde, 2-hydroxybutanal, 3-hydroxybutanal, 4-hydroxybutanal, bromomalonaldehyde and 2-(2-hydroxyethoxy)acetaldehyde;

a chelating agent selected from glutamic acid N,N-diacetic acid (GLDA), diethylene triamine pentaacetic acid (DTPA), imido disuccinic acid (IDS), L-aspartic acid diacetic acid (ASDA), ethylene diamine tetraacetic acid (EDTA), ethylene diamine disuccinic acid (EDDS), hydroxyethyl ethylenediaminetriacetic acid (HEDTA), citric acid and mixtures thereof; and an amine salt of a carboxylic acid wherein the carboxylic acid has 4 to 10 carbon atoms and the amine is compound of formula $R^1R^2R^3N$, wherein each of $R^1$, $R^2$ and $R^3$ is independently selected from hydrogen and an alkyl or hydroxyalkyl group having 1 to 6 carbon atoms, for example 1 to 4 carbon atoms.

In some preferred embodiments the composition of the second aspect comprises:

an aldehyde selected from 2-hydroxyhexanal, 2-hydroxyoctanal, 2-hydroxypropanal, glyceraldehyde, 2-hydroxybutanal, 3-hydroxybutanal, 4-hydroxybutanal, bromomalonaldehyde and 2-(2-hydroxyethoxy)acetaldehyde;

a chelating agent selected from glutamic acid N,N-diacetic acid (GLDA), diethylene triamine pentaacetic acid (DTPA), imido disuccinic acid (IDS), L-aspartic acid diacetic acid (ASDA), ethylene diamine tetraacetic acid (EDTA), ethylene diamine disuccinic acid (EDDS), hydroxyethyl ethylenediaminetriacetic acid (HEDTA), citric acid and mixtures thereof; and an amine salt of a carboxylic acid wherein the carboxylic acid has 4 to 10 carbon atoms and the amine is compound of formula $R'R^2R^3N$, wherein each of $R^1$, $R^2$ and $R^3$ is independently selected from hydrogen and an alkyl or hydroxyalkyl group having 1 to 6 carbon atoms, for example 1 to 4 carbon atoms.

In some preferred embodiments the method of the first aspect involves contacting the material with:

an aldehyde selected from 2-hydroxyhexanal and 2-hydroxyoctanal and 2-hydroxypropanal;

a chelating agent selected from glutamic acid N,N-diacetic acid (GLDA), diethylene triamine pentaacetic acid (DTPA) and mixtures thereof; and the diethanolamine or triethanolamine salt of octanoic acid or hexanoic acid.

In some preferred embodiments the composition of the second aspect comprises:

an aldehyde selected from 2-hydroxyhexanal and 2-hydroxyoctanal and 2-hydroxypropanal;

a chelating agent selected from glutamic acid N,N-diacetic acid (GLDA), diethylene triamine pentaacetic acid (DTPA) and mixtures thereof; and the diethanolamine or triethanolamine salt of octanoic acid or hexanoic acid.

In some preferred embodiments the method of the first aspect involves contacting the material with 2-hydroxyoctanal and GLDA.

In some preferred embodiments the composition of the second aspect comprises 2-hydroxyoctanal and GLDA.

In some especially preferred embodiments the method of the first aspect involves contacting the material with 2-hydroxyoctanal and the triethanolamine salt of octanoic acid.

In some preferred embodiments the composition of the second aspect comprises 2-hydroxyoctanal, GLDA and the triethanolamine salt of octanoic acid.

In some especially preferred embodiments the method of the first aspect involves contacting the material with 2-hydroxyoctanal, GLDA and the triethanolamine salt of octanoic acid.

In some preferred embodiments the composition of the second aspect comprises 2-hydroxyoctanal, GLDA and the triethanolamine salt of octanoic acid.

In one embodiment the composition of the second aspect comprises from 0.1 to 5 wt % of an aldehyde, from 0.1 to 5 wt % of a chelating agent and from 0.1 to 5 wt % of a salt of an amine and a carboxylic acid. The above amounts refer to the total amount of each component present in the composition.

In one preferred embodiment the composition of the second aspect comprises from 0.1 to 5 wt % 2-hydroxyoctanal, from 0.1 to 5 wt % GLDA and from 0.1 to 5 wt % of the triethanolamine salt of octanoic acid.

In some embodiments the composition may further comprise a crosslinking agent comprising two or more reactive moieties and a linker. Compounds of this type are described for example in US2015/034117 and US2015/0034119.

In some embodiments the reactive moieties are activated carboxylic acid or sulfonic acid derivatives and the linkers are polyamino compounds which may form salts or covalent bonds with the reactive moieties.

In some embodiments the reactive moieties are maleic acid derivatives and the linker has two or more amino groups linked by alkylene or oxyalkylene chains. The crosslinking agent may be a maleimide or a maleic acid amine salt.

In some embodiments the reactive moieties are maleic acid ions and the linker comprises quaternary ammonium ions linked by alkylene or oxyalkylene chains.

Some preferred crosslinking agents have the following structures:

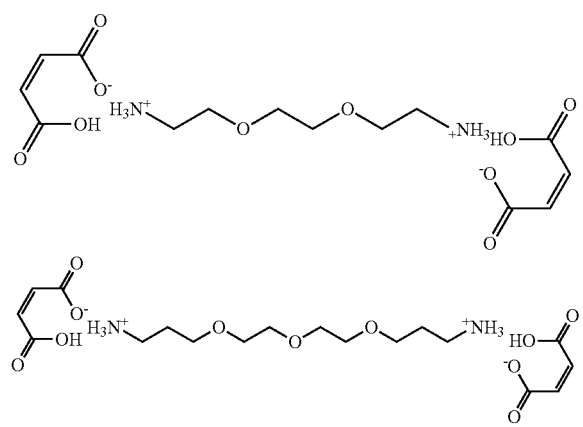

The crosslinking agent comprising two or more reactive moieties and a linker may be present in an amount of from 0.1 to 30 wt %, preferably 0.1 to 10 wt %, suitably 0.5 to 5 wt %.

The composition of the present invention may be provided in any suitable form. It may be in the form of a gel, paste, cream or wax. It may be in the form of a liquid composition. Such compositions may be in the form of a solution, dispersion or emulsion. It may be provided as a solid composition, for example as a powder or as a bar. In some embodiments a concentrate composition to be diluted prior to use may be provided. In some embodiments the composition of the second aspect may be part of precursor composition to be mixed with one or more further components prior to contact with the material.

The form and nature of the composition of the second aspect will depend on the intended use thereof.

In some embodiments the composition is a laundry detergent composition. In such embodiments the composition suitably comprises one or more further ingredients selected from builders, surfactants, chelating agents, bleaches, optical brighteners, enzymes, fragrances and other such ingredients commonly found in laundry detergent compositions. The composition may be a hand washing laundry detergent composition or an automatic laundry detergent composition.

In especially preferred embodiments the composition is a hair care composition.

The method of the first aspect of the present invention preferably provides a benefit to the material treated. Suitably the method enhances at least one property of the material that is treated according to the method.

In preferred embodiments the method is a method of treating hair that provides a beneficial effect to the hair. Suitably it enhances at least one property of the hair. Suitably the method of the first aspect involves contacting the hair with a composition of the second aspect.

The composition of the second aspect of the present invention is preferably a hair benefit composition. Suitably it enhances at least one property of the hair.

In some embodiments the composition and method of the present invention may provide a temporary change to a property of the hair, for example by providing increased shine or gloss, or improved softness or combability.

A temporary change in the property of the hair may be due to the composition coating the surface of the hair but forming a weak interaction such that the composition can be easily washed or brushed away.

In some preferred embodiments the composition and method of the present invention may provide a longer lasting benefit to the hair, for example a wash-durable benefit.

The composition and method of the present invention may be useful in permanent waving or straightening of the hair.

The composition and method of the present invention may improve the strength of the hair.

The composition and method of the present invention may prevent or inhibit loss of protein from the hair and/or they may be used to bind extra protein to the hair.

The composition and method of the present invention may provide protection to the hair against damage. For example the composition and method of the present invention may protect against damage from heat or sunlight.

In some embodiments the composition and method of the present invention may provide chemical resistance, for example protection against chlorine and other compounds found in swimming pools and the like.

Suitably the composition and method of the present invention may enhance at least one property of hair selected from shine, gloss, softness, combability, strength, straightness, waviness, thermal durability and UV stability.

Preferably the invention provides one or more benefits selected from increased and/or permanent/semi-permanent gloss or shine, improved and/or permanent/semi-permanent combability, improved and/or permanent/semi-permanent strength, increased and/or permanent/semi-permanent softness, reduced protein loss, improved thermal durability, increased chemical resistance, permanent/semi-permanent waviness and and/or permanent/semi-permanent straightness.

Suitably the composition comprises one or more diluents or carriers. Preferred diluents and carriers are cosmetically approved compounds and suitable examples of these will be known to the person skilled in the art. Examples of suitable carriers include organic solvents (eg, hydrocarbon solvents (eg, isododecane), alcohols (eg, ethanol, propanol and butanol), propylene carbonate, benzyl alcohol, aliphatic or aromatic esters (eg, vegetable oils, isopropyl myristate, C12-15 alkyl benzoate), perfluorocarbon solvents, and silicone fluids.

In some embodiments the composition is an aqueous composition. Suitably water is the major solvent present in the composition. In some embodiments water provides for at least 50 wt % of all solvents present in the composition, preferably at least 60 wt %, more preferably at least 70 wt %, suitably at least 80 wt %, for example at least 90 wt % or at least 95 wt %. In some embodiments one or more further water miscible solvents may be present. Examples of suitable water miscible solvents include monohydric and polyhydric alcohols, for example ethanol, glycerol and isopropanol.

In some embodiments the composition of the present invention is not aqueous and the major diluent or carrier is an oleophilic material. In such embodiments the composition may comprise as a major solvent one or more higher fatty alcohols, a mineral oil and/or a vegetable oil.

In some embodiments the composition is substantially aqueous but the aldehyde is dispersed within an oleophilic phase in which it is soluble.

In some embodiments the composition may consist essentially of one or more of an aldehyde and a succinimidyl ester and one or more of a chelating agent and a salt of an amine and a carboxylic acid and one more diluents or carriers. In preferred embodiments the composition comprises one or more further components. Suitable components are those typically used in personal care compositions and are known to the person skilled in the art.

As detailed above the compositions of the present invention may comprise different components depending on the intended use thereof. In some embodiments the composition may be used immediately after dyeing the hair. Alternatively the composition may be used one or more times as a hair treatment composition. In some embodiments it may be provided as a colour-loss prevention composition. Alternatively the composition may be in the form of shampoo, conditioner or hair styling product, for example a serum, wax, mousse, gel or spray or any other hair treatment form that could be used to provide general hair care benefits. Compositions which perform multiple functions, for example combined shampoo and conditioning compositions are also within the scope of the invention.

Suitably the composition comprises one or more additional components selected from surfactants, (including anionic, amphoteric, nonionic and cationic surfactants); conditioning agents (including quaternary ammonium compounds, cationic polymers, silicones, synthetic or natural oils or resins etc), fatty alcohols, electrolytes or other rheology modifiers, opacifying/pearlising agents, scalp benefit agents, fragrances, dyes, UV filters, penetration enhancers (eg, propylene carbonate, benzyl alcohol etc), preservatives, antioxidants, emulsifiers, pH adjusting agents and buffers and styling polymers (eg, polyvinylpyrrolidone etc).

In some embodiments the composition comprises a pH adjusting agent.

Suitable pH adjusting agents for use herein may include lactic acid, sodium hydroxide, sodium phosphate and salts and buffers thereof.

The pH of the composition will depend on the intended use thereof. However in preferred embodiments the composition has a pH of between 3 and 9, preferably between 3.5 and 8, more preferably between 4 and 7, preferably between 4 and 6.

In some preferred embodiments the composition is a hair care composition. Suitable hair care compositions include shampoo compositions, conditioning compositions, hair styling compositions and hair permanent waving, relaxing or permanent straightening compositions, or hair colouring compositions.

Suitable further ingredients and amounts thereof to be used in hair care compositions will be known to the person skilled in the art. The relative ratios of the components and the formulation of such compositions would be within the competence of the skilled person.

Suitably the composition is a substantially aqueous composition, suitably comprising at least 50 wt % water, preferably at least 60 wt %, more preferably at least 70 wt %.

Suitably the composition comprises one or more surfactants. For example the composition may comprise from 0.1 to 60 wt %, preferably 1 to 30 wt % surfactants, suitably from 5 to 25 wt %.

Suitably the composition comprises one or more anionic surfactants. For example the composition may comprise from 1 to 60 wt % anionic surfactants, preferably 1 to 30 wt %, suitably from 5 to 25 wt %.

In some embodiments the composition may comprise a quaternary ammonium salt, suitably in an amount of from 0.1 to 20 wt %, preferably 0.1 to 10 wt %.

In some embodiments the composition of the second aspect of the present invention is a shampoo composition.

Suitable shampoo compositions of the present invention may typically comprise 0.5 to 60 wt % of one or more anionic surfactants, preferably 1 to 50 wt %, more preferably 5 to 30 wt %, for example 8 to 20 wt % or 8 to 12 wt %; optionally from 0.1 to 30 wt % of amphoteric surfactants, preferably 1 to 15 wt %, for example 2 to 12 wt %; and optionally 0.1 to 40 wt % of non-ionic surfactants, preferably 0.5 to 30 wt %, for example 1 to 15 wt % or 2 to 12 wt %.

Shampoo compositions of the present invention may comprise one or more ingredients selected from anionic surfactants (eg, sodium laureth sulfate, sodium lauroyl methyl isethionate, sodium cocoyl methyl isethionate, sodium alpha-olefin sulfonate, sodium lauryl sulfoacetate, sodium monoalkyl phosphates, sodium dialkyl phosphates and sodium cocoyl methyl taurate, amphoteric surfactants (eg, cocamidopropyl betaine, sodium lauroamphoacetate, cocamidopropylhydroxy sultaine and disodium cocoamphodiacetate), foam boosters (eg, cocamide DEA, cocamide MEA, cocamide MIPA laureth-3), fatty alkyl alcohols (eg, cetyl alcohol, stearyl alcohol and behenyl alcohol), nonionic surfactants (eg, alkylpolyglucosides and alkyl ether ethoxylates), cationic polymers (eg, guar hydroxypropyl trimonium chloride, polyquaternium-10), silicones (eg, polydimethylsiloxanes such as dimethicone and dimethiconol), rheology modifiers (eg, carbomer, PEG-150 distearate and xanthan gum), synthetic or natural oils or resins (eg, mineral oil or vegetable oils), anti-dandruff agents (eg, piroctone olamine, zinc pyrithione and salicylic acid), styling agents (eg, polyisobutylene and polyvinyl pyrollidone/vinyl acetate copolymer), moisturising agents (eg, panthenol and glycerol), non-polymeric conditioning agents (eg, quaternary ammonium compounds such as behentrimonium chloride and stearalkonium chloride), opacifying/pearlising agents (eg, styrene/acrylates copolymer and ethylene glycol distearate), scalp benefit agents, fragrance, colouring agents, hair dyes, sunscreens, UV filters, preservatives, penetration enhancers (eg, propylene carbonate, benzyl alcohol etc) and diluents and carriers as defined herein.

Some preferred shampoo compositions of the present invention include 0.5 to 60 wt % of one or more anionic surfactants (for example, sodium laureth sulfate, sodium lauroyl methyl isethionate, sodium cocoyl isethionate, sodium alpha-olefin sulfonate, sodium lauryl sulfoacetate, sodium monoalkyl phosphates and sodium dialkyl phosphates); and 0 to 30 wt % of amphoteric surfactants (for example, cocamidopropyl betaine, sodium lauroamphoacetate and cocamidopropylhydroxy sultaine).

In some embodiments the composition of the second aspect of the present invention is a conditioning composition.

Suitable conditioning compositions of the present invention may typically comprise 0.1 to 20 wt % of one or more cationic surfactants, preferably 0.5 to 8 wt %, more preferably 1 to 4 wt %; and 0.1 to 20 wt % of one or more fatty alkyl alcohols, preferably 0.5 to 8 wt %, more preferably 1 to 4 wt %; and optionally 0.1 to 20 wt % of one or more non-ionic surfactants, preferably 0.5 to 8 wt %, more preferably 1 to 4 wt %; and optionally 0.1 to 20 wt % of one or more cationic polymers, preferably 0.5 to 8 wt %, more preferably 1 to 4 wt %.

Conditioning compositions of the present invention including rinse-off and leave-on conditioners (including 'hair masks') and hair shine or appearance enhancing products, anti-frizz treatment serums and other treatments, either leave-in or rinse-off, designed to be applied to the hair immediately after colouring or any time thereafter, and hair-tonics. Such compositions may comprise one or more further ingredients selected from: cationic surfactants including mono- and di-fatty alkyl tertiary amines and quaternary ammonium compounds (eg, mono- and di-fatty alkyl quaternary ammonium compounds, such as cetrimonium chloride, steartrimonium chloride and behentrimonium chloride), fatty alkyl alcohols (eg, cetyl alcohol, stearyl alcohol and behenyl alcohol), nonionic surfactants (eg, alkylpolyglucosides and alkyl ether ethoxylates, eg, ceteareth-20), cationic polymers (eg, guar hydroxypropyl trimonium chloride, polyquaternium-10), silicones (eg, polydimethylsiloxanes such as dimethicone and dimethiconol), rheology modifiers (eg, hydroxyethyl cellulose and polyquaternium-37), moisturising agents (eg, panthenol and glycerol), non-polymeric conditioning agents (eg, quaternary ammonium compounds such as behentrimonium chloride and stearalkonium chloride), scalp benefit agents, fragrance, colouring agents, hair dyes, sunscreens, UV filters preservatives, penetration enhancers (eg, propylene carbonate, benzyl alcohol etc), and diluents and carriers as defined herein.

Some preferred conditioning compositions of the present invention include 0.1 to 20 wt % of cationic surfactants (for example, mono- and di-fatty alkyl quaternary ammonium compounds, mono- and di-fatty alkyl tertiary amines), 0.1% to 20 wt % of fatty alkyl alcohols; and 0.1% to 20 wt % of non-ionic surfactants (for example, ceteareth-20).

In some embodiments the composition of the second aspect of the invention is a hair styling composition.

Suitable hair styling compositions of the present invention may typically comprise from 0.1 to 40 wt % of one or more hair styling polymers, preferably from 0.1 to 30 wt %, more preferably from 0.5 to 10 wt %.

Hair styling compositions of the present invention (including gels, mousses with and without propellant, hair sprays with and without propellant, hair pomades, hair waxes, hair creams, hair brilliantines and compositions designed to be used in conjunction with heated styling appliances such as blow dryers, curling tongs, straightening irons, hot air hoods (as used for example in hair salons)) may comprise one or more further ingredients selected from: hair styling polymers (eg, polyvinylpyrrolidone, polyvinylpyrrolidone/vinyl acetate copolymers, octylacrylamide/acrylates/butylaminoethyl methacrylate copolymer, methyl vinyl ether/maleic anhydride copolymers and polyethylene waxes), rheology modifiers (eg, carbomers, acrylates copolymers, hydroxyethylcellulose, xanthan gum and polyquaternium-37), aminomethyl propanol, fatty alkyl alcohols (eg, cetyl alcohol, stearyl alcohol and behenyl alcohol), ethanol, propyl alcohol, isopropyl alcohol, petrolatum, mineral oil, ozokerite, beeswax, carnauba wax, silicones (eg, polydimethylsiloxanes such as dimethicone and dimethiconol), polyethylene glycols, anionic surfactants (eg, sodium laureth sulfate and sodium lauroyl methyl isethionate), amphoteric surfactants (eg, cocamidopropyl betaine and disodium cocoamphodiacetate), nonionic surfactants (eg, alkylpolyglucosides and alkyl ether ethoxylates), cationic polymers (eg, guar hydroxypropyl trimonium chloride, Polyquaternium-10), silicones (eg, polydimethylsiloxanes such as dimethicone and dimethiconol), moisturising agents (eg, panthenol and glycerol), non-polymeric conditioning agents (eg, quaternary ammonium compounds such as behentrimonium chloride and stearalkonium chloride), scalp benefit agents, fragrance, colouring agents, hair dyes, sunscreens, UV filters, preservatives, penetration enhancers (eg, propylene carbonate, benzyl alcohol etc), and diluents and carriers as defined herein.

Some preferred hair styling compositions of the present invention include 0.1 to 40 wt % of one or more hair styling polymers/resins (for example, polyvinylpyrrolidone, polyvinylpyrrolidone/vinyl acetate copolymers, octylacrylamide/acrylates/butylaminoethyl methacrylate copolymer, methyl vinyl ether/maleic anhydride copolymers and polyethylene waxes).

Those skilled in the art will appreciate that it is possible to confer one or more attributes of hair conditioning, shine etc, and hair styling to the hair from a single product containing the appropriate ingredients thus, compositions having such combinations of hair benefit effects are also covered in the invention.

In some embodiments the composition of the second aspect is a hair permanent waving composition.

Suitable hair permanent waving compositions of the present invention may typically comprise 0.1 to 20 wt % of one or more reducing agents, preferably from 0.5 to 15 wt %, more preferably 3 to 12 wt %.

Some preferred hair permanent waving compositions of the present invention include 0.5 to 15 wt % of one or more reducing agents (for example, as thioglycolic acid, ammonium thioglycolate, thiolactic acid, cysteamine, cysteine, glycerol monothioglycolate, sodium sulphite/bisulfite); alkalising agents (for example, ammonia, monoethanolamine) in an amount sufficient to adjust the pH of the reducing component to between pH 8-13. Hair permanent waving compositions are typically provided in a package with a second composition comprising 0.5 to 10 wt % of one or more oxidising agents (for example, hydrogen peroxide, sodium bromate, sodium percarbonate and sodium perborate) which are applied after the reducing agent composition has been applied, allowed to process and then rinsed off.

In some embodiments the composition of the second aspect of the present invention is a hair relaxing composition.

Hair relaxing compositions of the present invention may include one or more ingredients selected from sodium hydroxide, lithium hydroxide, potassium hydroxide, calcium hydroxide and guanidine carbonate. These components are suitably present in an amount of from 0.5 to 5 wt %.

Other types of permanent straightening compositions may include one or more ingredients selected from formaldehyde, glycoxylic acid, glutaraldehyde and glyoxyloyl carbocysteine. These components are suitably present in an amount of from 0.1 to 10 wt %.

The hair permanent waving, relaxing and permanent straightening compositions mentioned above may further include one or more additional ingredients selected from anionic surfactants (eg, sodium laureth sulfate and sodium lauroyl methyl isethionate), amphoteric surfactants (eg, cocamidopropyl betaine and disodium cocoamphodiacetate), quaternary ammonium compounds (eg, cetrimonium chloride, steartrimonium chloride and behentrimonium chloride), fatty alkyl alcohols (eg, cetyl alcohol, stearyl alcohol and behenyl alcohol), nonionic surfactants (eg, alkylpolyglucosides and alkyl ether ethoxylates), cationic polymers (eg, guar hydroxypropyl trimonium chloride, polyquaternium-10), silicones (eg, polydimethylsiloxanes such as dimethicone and dimethiconol), opacifying agents (eg, styrene acrylates copolymer), rheology modifiers (eg, hydroxyethyl cellulose and xanthan gum), moisturising agents (eg, panthenol and glycerol), non-polymeric conditioning agents (eg, quaternary ammonium compounds such as behentrimonium chloride and stearalkonium chloride), fragrance, sunscreens, UV filters, colouring agents and diluents and carriers as defined herein.

In some embodiments the composition of the second aspect of the present invention is a hair colouring composition.

Hair colouring compositions may include a dye compound and/or may include a dye precursor compound which forms an active dye in the hair in situ following admixture with an oxidising composition.

Oxidative hair colouring compositions of the present invention may include one or more intermediates, for example p-phenylenediamine, N,N-bis(2-hydroxyethyl)-p-phenylenediamine, p-toluenediamine, p-aminophenol, phenyl methyl pyrazolone, m-phenylenediamine, resorcinol, 1-naphthol, 1-hydroxyethyl 4,5-diamino pyrazole and m-aminophenol. These intermediates can be present in any combination and ratios at a total intermediate concentration of from 0.01% to 15%, depending upon the desired shade. Such compositions typically further include one or more alkalising agents, for example ammonia, ammonium hydroxide, sodium hydroxide and monoethanolamine. Developer compositions for oxidative dyeing include an oxidising agent, for example hydrogen peroxide, sodium bromate, sodium percarbonate or sodium perborate. These are typically present in an amount of from 0.1 to 30 wt %.

Direct-dye colour compositions of the present invention may include one of more direct dyes for example from the classes of nitrophenylenediamines (eg, 4-nitro-o-phenylenediamine etc), nitroaminophenols (eg, 2-amino-4-nitrophenol etc) and aminoanthraquinones (eg, Disperse Red 11 etc). These are typically present in an amount of 0.1 wt % to 20 wt %, depending on the desired shade.

In some preferred embodiments the composition of the present invention is not a hair colouring composition. Preferably the composition comprises less than 0.1 wt %, preferably less than 0.01 wt % of dye compounds and/or dye precursor compounds. Preferably the composition does not comprise dye compounds and/or dye precursor compounds. Compounds which provide colour to the composition such as pigments and pearlescent agents may be present but suitably the composition does not include any compounds which may be used to dye hair.

In the method of the first aspect the material is contacted with an electrophilic species selected from aldehydes, succinimidyl esters and mixtures thereof; and a chelating agent and/or a salt of an amine and a carboxylic acid.

The material, preferably hair, may be wet or dry when contacted with the composition.

Suitably the composition is applied to the material and spread across the surface of the material. In preferred embodiments in which the material is hair the composition may be rubbed into the hair in the manner of a shampoo and/or it may be combed through the hair.

The composition of the present invention may be left on the material or it may be removed from the material. Suitably it may be rinsed using warm water.

In some embodiments the composition may be contacted with the material, spread throughout and then immediately removed.

Suitably the composition may be removed from the material by rinsing, preferably by using water.

In some embodiments the composition may be washed from the material by washing with a detergent composition.

In some embodiments the composition may be mechanically removed from the material, for example by brushing.

In some embodiments the composition may be left on the material and not removed until the material is washed during a normal cycle.

In some embodiments in which the material is hair, the composition may be applied to the hair, spread throughout and rubbed into the hair, and then rinsed with water, in the manner of a shampoo.

In some embodiments in which the material is hair, the composition may be applied to the hair, spread throughout the hair (optionally with combing), left on the hair for a short period and then rinsed from the hair with water, in the manner of a conditioner.

In some embodiments in which the material is hair, the composition may be contacted with the hair and left on the hair in the manner of a styling product. The composition may be sprayed throughout the hair, rubbed throughout the hair, combed throughout the hair or otherwise spread through the hair in a manner known to those skilled in the art.

In embodiments in which the composition is left on the hair, it suitably remains on the hair until the hair is next washed, although some of the composition may be brushed out or rubbed away during normal activity.

In the method of the present invention the composition is suitably contacted with the material, preferably hair, at ambient temperature. In some embodiments the composition may be contacted with the material at a temperature greater than the ambient temperature.

In some embodiments the composition may be contacted with the hair and the hair carrying the compositions is then heated and/or manipulated and/or dried. Thus the hair may be dried using a hairdryer or straightened after the composition is applied.

The methods of the first and second aspect of the present invention may involve heating the hair. Such a heating step may involve commonly used heating techniques such as blow drying, or using tongs, straighteners or hoods etc.

The present invention may involve contacting the material with a composition comprising an aldehyde and/or succinimidyl ester and chelating agent and/or amine salt once or more than once.

The invention may be used on a regular basis, for example every time hair (or another material) is washed. Alternatively the invention may be used periodically on a less frequent basis, for example, every week or every month.

It has been surprisingly found that the method of the present invention can significantly benefit the hair. This benefit may be a temporary benefit, a permanent benefit or a semi-permanent benefit.

The method and composition of the present invention may benefit the hair by providing improved shine.

The method and composition of the present invention may benefit the hair by providing improved strength.

The method and composition of the present invention may benefit the hair by providing improved thermal protection.

The method and composition of the present invention may benefit the hair by providing permanent waving or straightening under mild conditions.

The method and composition of the present invention may benefit the hair by providing improved manageability and/or combability.

According to a fourth aspect of the present invention there is provided the use of an electrophilic species selected from aldehydes, succinimidyl esters and mixtures thereof and one or more of a chelating agent and/or a salt of an amine and a carboxylic acid to enhance at least one property of hair. Preferred features of the third aspect are as defined in relation to the first and second aspects.

The invention will now be further described with reference to the following non-limiting examples:

EXAMPLE 1

The hydroxy-substituted aldehyde compounds used in the present invention were prepared using the following method:

These are formed from corresponding 1,2-diol compounds by selective oxidation of the alpha alcohol. In a three necked flask, a copper catalyst in a high temperature oil were weighed. The flask was then fitted with side arm, a receiving flask and a water cooled condenser. The reaction was heated with stirring to the correct temperature under a flow of nitrogen and/or vacuum.

The required alcohol was added continuously at a constant rate. The product was collected by distillation from the reaction mixture. The vacuum or nitrogen was adjusted to ensure the aldehyde was distilled over rapidly to reduce the chance of further oxidation. The exact conditions depend on aldehyde being produced. A yield of greater than 75% is typical.

EXAMPLE 2

Wool swatches were dyed with an oxidative red dye formed as follows:

The dyed swatches were immersed in an aqueous solution comprising the test compounds listed in table 1 in the specified amounts and 0.1 wt % SLES buffered to pH 5.5 with sodium acetate buffer for 30 minutes at 40° C. The swatches were then rinsed in water for 2 minutes and then dried. The reading of the colour intensity of the resultant cloth was measured using standard reflectometry and compared with a deionised water control (containing 0.1 wt % SLES). In this case the difference in reflectance of light having a wavelength of 457 nm was measured.

The results in table 1 are the absolute values of $\Delta R457$ wherein $\Delta R457$ is the difference in reflectance at 457 nm between the initially dyed wool swatches and the swatches that have been treated as detailed in the table.

TABLE 1

| | Amount in wt % | | | |
|---|---|---|---|---|
| Composition | 2-hydroxyoctanal | GLDA** | Amine salt* | $\Delta R457$ |
| 1 | 0.00 | 0.00 | 0.00 | 6.1 |
| 2 | 0.00 | 1.25 | 0.50 | 3.6 |
| 3 | 0.50 | 1.18 | 0.54 | 2.1 |
| 4 | 1.00 | 1.27 | 0.24 | 2.3 |
| 5 | 0.50 | 1.25 | 0.00 | 4 |
| 6 | 0.82 | 0.04 | 0.50 | 3.7 |

*The amine salt used in the examples was the triethanolamine salt of octanoic acid.
**The amount refers to the amount as free acid.

EXAMPLE 3

The tests of example 2 were repeated except the components were added to an aqueous composition comprising 10 wt % of a commercial shampoo formulation rather than 0.1 wt % SLES.

The results in table 2 are the absolute values of $\Delta R457$ wherein $\Delta R457$ is the difference in reflectance at 457 nm between the initially dyed wool swatches and the swatches that have been treated as detailed in the table.

TABLE 2

| Composition | Amount in wt % | | | ΔR457 |
| --- | --- | --- | --- | --- |
| | 2-hydroxyoctanal | GLDA** | Amine salt* | |
| 1 | 0.00 | 0.00 | 0.00 | 5.9 |
| 2 | 0.00 | 1.25 | 0.50 | 3.8 |
| 3 | 0.00 | 2.50 | 0.50 | 2.4 |
| 4 | 0.26 | 0.00 | 0.49 | 4.9 |
| 5 | 0.50 | 1.25 | 0.00 | 2.5 |
| 6 | 0.50 | 2.50 | 0.50 | 1.2 |
| 7 | 0.54 | 1.18 | 0.54 | 3.3 |
| 8 | 1.00 | 1.25 | 0.80 | 0.5 |
| 9 | 1.00 | 1.27 | 0.24 | 2.2 |
| 10 | 1.00 | 2.50 | 0.00 | 1.4 |
| 11 | 1.00 | 2.50 | 1.00 | 0 |

*The amine salt used in the examples was the triethanolamine salt of octanoic acid.
**The amount refers to the amount as free acid.

EXAMPLE 4

The permanent/semi-permanent hair straightening effect of compositions comprising 2-hydroxyoctanal or the triethanolamine salt of octanoic acid was assessed as follows:

Method
1. 15.2 cm/3 g bleached straight hair tresses were pre-washed with a standard commercial non-conditioning shampoo, combed, hung vertically and allowed to air dry for six hours under ambient conditions, then their initial lengths were measured.
2. For the 'treated' hair tresses, 2 ml of an aqueous solution containing
   (a) 2% w/w of the triethanolamine salt of octanoic acid and 1% w/w of SLES; or
   (b) 2% w/w of 2-hydroxyoctanal and 1% w/w of SLES; was applied to the hair tresses, combed through and left to stand for 5 minutes.
3. For the control hair tresses, 2 ml of an aqueous solution containing 1% w/w of SLES was applied to the hair tresses, combed through and left to stand for 5 minutes.
4. The hair tresses were flat ironed with a Tormaline® ceramic hot iron, passing it over the tresses slowly five times.
5. The hair tresses were washed and rinsed thoroughly to remove non-bound material from the hair.
6. The hair tresses were combed straight, hung vertically, and allow to air dry for six hours under ambient conditions.
7. The final length of the hair tresses was measured.
8. The degree of straightening was calculated according to the following equation:

$$\% \text{ Straightening} = \frac{L2 - L1}{L0 - L1} \times 100\%$$

Where:
L0=Total straightened length of hair tress
L1=Initial untreated compressed curly length of tress
L2=Final length of tress after straightening, wash, and air dry.

Results
After treatment of the tresses, the degree of straightening was as follows:
(a) 64.2 (±8.8)% (average of three hair tress replicates)
(b) 79.2 (±5.9)% (average of three hair tress replicates)
compared to 21.2 (±9.5)% (average of three hair tress replicates) of that of the control tresses. This indicates a permanent/semi-permanent hair straightening effect was conferred. This is believed to be due to reaction of the hair with the triethanolamine salt of octanoic acid (a) or 2-hydroxyoctanal (b).

The invention claimed is:

1. A hair care composition comprising an electrophilic species selected from the group consisting of aldehydes, succinimidyl esters and mixtures thereof; and a chelating agent and/or a salt of an amine and a carboxylic acid; wherein the aldehyde is a hydroxyl aldehyde having a single hydroxyl substituent, said single hydroxyl substituent located at a 2, 3 or 4 position of said aldehyde, and wherein the succinimidyl ester is a compound of formula (IV):

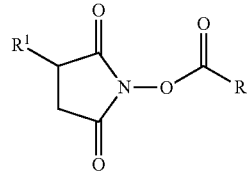

wherein R is phenyl or $CH_3(CH_2)_n$ wherein n is 5 to 10; and $R^1$ is hydrogen or a sulfonate moiety.

2. The composition according to claim 1 wherein the aldehyde is an alpha-substituted aldehyde.

3. The composition according to claim 1 wherein the aldehyde is selected from the group consisting of 2-hydroxypropanal, 2-hydroxyhexanal, and 2-hydroxyoctanal.

4. The composition according to claim 1 comprising a first aldehyde having less than 10 carbon atoms and a second aldehyde having 10 or more carbon atoms.

5. The composition according to claim 4 wherein the second aldehyde is selected from the group consisting of 2-hydroxydecanal, 2-hydroxydodecanal and 2-hydroxytetradecanal.

6. The composition according to claim 4 wherein the first aldehyde is selected from the group consisting of 2-hydroxyhexanal, 2-hydroxyoctanal, 2-hydroxypropanal, glyceraldehyde, 2-hydroxybutanal, 3-hydroxybutanal, 4-hydroxybutanal, bromomalonaldehyde, 2-(2-hydroxyethoxy) acetaldehyde, 2-chloro octanal, 2-fluoro octanal, 2-bromo octanal, 6-hydroxyhexanal, 3-hydroxypropanal and 4-hydroxy-but-2-enal and the second aldehyde is selected from the group consisting of 2-hydroxydecanal, 2-hydroxydodecanal and 2-hydroxytetradecanal.

7. The composition according to claim 1 wherein the chelating agent is a polycarboxylic acid derived chelating agent.

8. The composition according to claim 1 wherein the chelating agent is selected from the group consisting of diethylene triamine pentaacetic acid (DTPA), glutamic acid N, N-diacetic acid (GLDA) and mixtures thereof.

9. The composition according to claim 1 wherein the amine salt of a carboxylic acid is an amine salt of a carboxylic acid wherein the carboxylic acid has 4 to 10 carbon atoms.

10. The composition according to claim 9 wherein the amine salt is the diethanolamine salt or triethanolamine salt of octanoic acid or hexanoic acid.

11. The composition according to claim 1 which is selected from a shampoo composition, a conditioning composition, a hair styling composition, a hair permanent waving composition, a hair relaxing composition, a hair permanent straightening composition and a hair colouring composition.

12. The composition according to claim 1 which further comprises 1 to 30 wt % surfactants.

13. The composition according to claim 1 which further comprises a crosslinking agent comprising two or more maleic acid derived reactive moieties and a linker having two or more amino groups.

14. The composition according to claim 1 which provides one or more benefits selected from the group consisting of increased gloss or shine, improved combability, improved strength, increased softness, reduced protein loss, improved thermal durability, increased chemical resistance, increased waviness and increased straightness.

15. The composition according to claim 14 wherein the benefit may be temporary, semi-permanent or permanent.

16. A packaged hair colouring product comprising one or more compositions wherein the one or more compositions comprise at least one dye compound and/or one dye precursor compound; and the hair care composition of claim 1.

* * * * *